(12) United States Patent
Sekiguchi et al.

(10) Patent No.: US 7,932,276 B2
(45) Date of Patent: Apr. 26, 2011

(54) AGENT FOR CURING CHRONIC OBSTRUCTIVE PULMONARY DISEASE

(75) Inventors: Kazuo Sekiguchi, Kitajima (JP); Katsumi Ikezono, Aizumi (JP); Kazuhide Ohta, Tokushima (JP); Takashi Maeda, Kitajima (JP); Hisashi Nagamoto, Matsushige (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 546 days.

(21) Appl. No.: 11/760,345

(22) Filed: Jun. 8, 2007

(65) Prior Publication Data

US 2008/0081828 A1 Apr. 3, 2008

Related U.S. Application Data

(63) Continuation of application No. 10/478,471, filed as application No. PCT/JP02/07221 on Jul. 16, 2002, now abandoned.

(30) Foreign Application Priority Data

Jul. 24, 2001 (JP) ................................. 2001-222768

(51) Int. Cl.
*A01N 43/78* (2006.01)
*A61K 31/425* (2006.01)
*C07D 277/60* (2006.01)
*C07D 417/00* (2006.01)

(52) U.S. Cl. ....................................... 514/366; 548/150

(58) Field of Classification Search .................. 514/366; 548/150

See application file for complete search history.

(56) References Cited

U.S. PATENT DOCUMENTS

2003/0013712 A1* 1/2003 Tullis et al. .................. 514/241

FOREIGN PATENT DOCUMENTS

EP 0513387 A1 11/1992
JP 5051318 A 3/1993

OTHER PUBLICATIONS

Hanania, N.A. "Inflammation in COPD: Can Anything Be Done?", Medscape, Jun. 30, 2005.*
Ohnishi et al. "Generation of tumor necrosis factor alpha by human nasal epithelial cells and inhibition by fluticasone propionate" Arerugi, Oct. 1995, pp. 1216-22; abstract provided.*
Cazzola et al. "Additive Effects of Salmeterol and Fluticasone or Theophylline in COPD", Chest, 2000, vol. 118, pp. 1576-1581.*
Translation of the Office Action issued in the corresponding Egyptian application.

* cited by examiner

*Primary Examiner* — Sreeni Padmanabhan
*Assistant Examiner* — Kendra D Carter
(74) *Attorney, Agent, or Firm* — Finnegan, Henderson, Farabow, Garrett & Dunner, L.L.P.

(57) ABSTRACT

The present invention provides a useful and highly safe agent for the treatment of chronic obstructive pulmonary disease, which contains, as the effective ingredient, at least one compound selected from the group consisting of thiazole derivatives and salts thereof represented by the general formula (1),

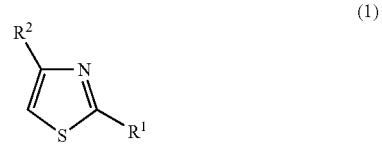

(1)

wherein, $R^1$ is a phenyl group which may have 1 to 3 lower alkoxy groups as the substituents on the phenyl ring; $R^2$ is a pyridyl group which may have 1 to 3 carboxyl groups as the substituents on the pyridine ring.

2 Claims, No Drawings

AGENT FOR CURING CHRONIC OBSTRUCTIVE PULMONARY DISEASE

This is a continuation of application Ser. No. 10/478,471, filed Nov. 21, 2003, now abandoned which is a U.S. National Phase of International Application No. PCT/JP02/07221, filed Jul. 16, 2002, which claims priority to JP 2001-222768 filed Jul. 24, 2001, all of which are incorporated herein by reference.

TECHNICAL FIELD

The present invention relates to an agent for the treatment of chronic obstructive pulmonary disease.

BACKGROUND ART

Chronic obstructive pulmonary disease (COPD) is characterized by the progressive development of airflow limitation (airway obstruction) (Pauwell R. A., et al.: Am. J. Respir. Crit. Care Med., 2001 (163), 1256-1276).

COPD is one of the major causes of chronic morbidity and mortality throughout the world, and in the Asia-Pacific region, it is also foreseen that patients of COPD will rapidly increase within about 20 years from now on, due to the growth of smokers and the aging population.

A diagnosis of COPD should be considered in smokers who have clinical symptoms and signs, such as progressive developing abnormal shortness of breath, associated with airflow obstruction. For this reason, every country in the world has been paying much attention to diagnosis and treatments of COPD.

At present, as to drug therapy for the treatment of COPD, certain drugs such as $\beta_2$-stimulants, anticholinergic agents and the like, having bronchodilatory action are tentatively used for preventing or suppressing the symptoms. However, these drugs having bronchodilatory action cannot exhibit an improvement in deterioration of the pulmonary function for long period of time, which is the characteristic of COPD and the most important clinical index.

Regarding the effect of steroids, having potent inhibitory effect on the production of cytokines, as an inhalant have been assessed in plural clinical studies in large scale. However, most of them also showed that steroids could not improve the deterioration of the pulmonary function for long period of time (Pauwels R. A., Lodahl C. G., Laitinen L. A., Schouten J. P., Postma D. S., Pride N. B., et al: N. Engl. J. Med., 1999 (340), 1948-1953; Vestbo J., Sorensen T., Lange P., Brix A., Torre P., Viskum K.: Lancet, 1999 (353), 1819-1823; Burge P. S., Calverley P. M., Jones P. W., Spencer S., Anderson J. A., Maslen T. K.: BMJ, 2000 (320), 1297-1303)).

Regarding the drugs having inhibitory effect on the production of active oxygen, any reliable clinical studies have not been examined as yet.

N-acetylcystein is an antioxidant having a similar effect to that of agents having inhibitory action on the production of active oxygen. While, clinical study showed that N-acetylcystein could reduce the acute exacerbation rate of COPD (C. Stey, J. Steure, S. Bachmann, T. C. Medici, M. R. Tramer; Eur. Respir. J., 2000, (16), 253-262). However, there are no reports at all, that N-acetylcystein shows to improve the deterioration of the pulmonary function in COPD patients for long period of time.

Furthermore, clinical studies are conducting to examine whether the drugs inhibiting phosphodiesterase IV activity will be the treatment of COED. However, it has been reported that these drugs have adverse side-effects as well, for example, nausia, vomiting and increasing the secretion of acid in the stomach (Peter J. Barnes: N. Engl. J. Med., 2000 (343) No. 4, 269-280).

As is explained above, there are no drugs having improvement in deterioration of the pulmonary function in CCPD, as well as having sufficient ability as a drug for the treatment of COPD, which have yet been developed.

DISCLOSURE OF THE INVENTION

An object of the present invention is to provide a useful and highly safe drug for the treatment of COPD.

The present inventors have prepared an animal model having the pathogenic features, which is clinically very close to COPD, and have conducted extensive research works by use of this animal model. As the result, the inventors have found the facts that some of thiazole derivatives, which are disclosed in JP-A-5-51318, JP-A-10-152437, EP 513387 A1 and WO98/14191, known as inhibitors for producing active oxygen, producing cytokines and cell adhesion, possess improving effects on the deterioration of the pulmonary function, such as airflow obstruction, thus such thiazole derivatives exhibit extremely high effect for curing COPD with lesser side effects like nausia, vomiting and secretion of acid in the stomach with high safety. Finally, the present invention has been completed on the basis of these findings.

1) The present invention relates to an agent for the treatment of COPED characterized by containing, as the effective ingredient, at least one compound selected from the group consisting of thiazole derivatives and salts thereof represented by the general formula (1),

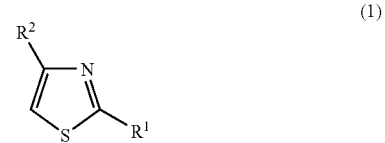

(1)

wherein $R^1$ is a phenyl group which may have 1 to 3 lower alkoxy groups on the phenyl ring; and $R^2$ is a pyridyl group which may have 1 to 3 carboxyl groups on the pyridine ring.

(2) The present invention relates to the agent for the treatment of COPD as mentioned in the above 1), wherein the thiazole derivative is 6-[2-(3,4-diethoxyphenyl)thiazol-4-yl]pyridine-2-carboxylic acid.

BEST MODE FOR CARRYING OUT THE INVENTION

The thiazole derivatives represented by the general formula (1) of the present invention are known compounds, and can be prepared by the methods for example, the method disclosed in JP-A-5-51318.

Each one of the groups in the above-mentioned general formula (1) is specifically mentioned as follows.

As for a phenyl group which may have 1 to 3 lower alkoxy groups as the substituents on the phenyl ring, there can be exemplified a phenyl group which may have 1 to 3 straight- or branched-chain alkoxy groups having 1 to 6 carbon atoms, as the substituents on the phenyl ring, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 3-ethoxy-4-methoxyphenyl, 4 hexyloxyphenyl, 3,4-dimethoxyphenyl, 3,4-diethoxyphenyl, 2,3-dimethoxyphenyl, 2,6-dimethoxyphenyl, 3-propoxy-4-methoxyphenyl, 3,5-dimethoxyphenyl, 3,4-dipentyloxyphenyl, 3,4,5-trimehoxyphenyl, 3-methoxy-4-ethoxyphenyl groups and the like.

As for a pyridyl group which may have 1 to 3 carboxyl groups as the substituents on the pyridine ring, there can be exemplified a pyridyl group which may have 1 to 3 carboxyl groups as the substituents on the pyridine ring, such as pyridyl, 2-carboxylpyridyl, 3-carboxylpyridyl, 4-carboxylpyridyl, 2,3-dicarboxylpyridyl, 3,4-dicarboxylpyridyl, 2,4-dicarboxylpyridyl, 3,5-dicarboxylpyridyl, 3,6-dicarboxylpyridyl, 2,6-dicarboxylpyridyl, 2,4,6-tricarboxylpyridyl and the like.

Among the thiazole derivatives represented by the general formula (1) of the present invention, a compound having basic groups can form a salt thereof with pharmacologically acceptable acids. As to such acids, there can be exemplified inorganic acids such as sulfuric acid, nitric acid, hydrochloric acid, phosphoric acid, hydrobromic acid and the like; and organic acids such as acetic acid, p-toluenesulfonic acid, ethanesulfonic acid, oxalic acid, maleic acid, fumaric acid, malic acid, tartaric acid, citric acid, succinic acid, benzoic acid and the like.

Among the thiazole derivatives represented by the general formula (1) of the present invention, a compound having acidic groups can form a salt thereof with pharmacologically acceptable basic compounds. As to such basic compounds, there can be exemplified sodium hydroxide, potassium hydroxide, calcium hydroxide, sodium carbonate, potassium hydrogen carbonate and the like.

The thiazole derivatives of the present invention include their optical isomers.

Generally, a compound represented by the general formula (1) is used in the forms of common pharmaceutical preparations.

The pharmaceutical preparations are prepared with conventional diluents or excipients such as fillers, diluents, binders, wetting agents, disintegrators, surface active agents, lubricants and the like.

As to the pharmaceutical preparations desired unit forms can be selected depending on the curing purposes. Typical unit forms include tablets, pills, powders, liquids, suspensions, emulsions, granules, capsules, suppositories, injections (liquids, suspensions, etc.), inhalants and the like can be exemplified.

For shaping in tablet form preparation, any carriers widely used in this field can be used. Examples of carriers include excipients such as lactose, white sugar, sodium chloride, glucose, urea, starch, calcium carbonate, kaolin, crystalline cellulose and silicic acid; binder such as water, ethanol, propanol, simple syrup, glucose, starch solution, gelatin solution, carboxymethyl cellulose, shelac, methyl cellulose, potassium phosphate and polyvinyl pyrrolidone; disintegrators such as dried starch, sodium alginate, agar-agar powder, laminaran powder, sodium hydrogen carbonate, calcium carbonate, fatty acid esters of polyoxyethylene sorbitan, sodium laurylsulfate, monoglyceride of stearic acid, starch and lactose; disintegration inhibitors such as white sugar, stearin, cacao butter and hydrogenated oil; absorption accelerators such as quaternary ammonium base and sodium laurylsulfate; wetting agents such as glycerin and starch; adsorbing agents such as starch, lactose, kaoline, bentonite and colloidal silicic acid; lubricants such as refined talc, stearic acid salts, boric acid powder and polyethylene glycol. If necessary, tablets can be further coated with usual coating materials to make them as sugar coated tablets, gelatin film coated tablets, tablets coated with enteric coatings, tablets coated with films, double layered tablets and multiple layered tablets.

For the purpose of shaping the pharmaceutical composition in the form of pills, any excipients which are known and widely used in this field can be used, for example, carriers such as glucose, lactose, starch, cacao butter, hardened vegetable oils, kaolin, talc and the like; binders such as arabic gum powder, powdered tragacanth, gelatin, ethanol and the like; disintegrating agents such as laminaria, agar-agar and the like.

For the purpose of shaping the pharmaceutical composition in the form of suppositories, any excipients which are known and widely used in this field can be used, for example, polyethylene glycols, cacao butter, higher alcohols, esters of higher alcohols, gelatin, semi-synthesized glycerides and the like.

For the purpose of shaping the pharmaceutical composition in the form of capsules, they are prepared in accordance with a conventional method by mixing the effective ingredient with the above-mentioned various carriers, then filling it in hard gelatin capsules or soft gelatin capsules.

For the purpose of shaping the pharmaceutical composition in the form of injection preparations, solutions emulsions and suspensions are sterilized and are preferably made isotonic to the blood. In making the injection preparations, any diluents usually used in this field can be used, for example, water, ethyl alcohol, polyethylene glycol, propylene glycols, ethoxylated isostearyl alcohol, polyoxylated isostearyl alcohol, polyoxyethylene sorbitan fatty acid esters and the like. In these instances, an adequate amount of sodium chloride, glucose or glycerin may be added to the desired injection preparations to make them isotonic to the blood. Further, usual dissolving auxiliaries, buffering agents, analgesic agents may be added. Yet further, if necessary, coloring agents, preservatives, perfumes, seasoning agents, sweetening agents and other medicines may be added to the desired pharmaceutical preparations.

Inhalant compositions are prepared in accordance with usual methods. That is, the effective ingredients are made in powder or liquid form, and formulated with an inhalation propellant and/or carrier, then filled in a suitable inhalation container. Further, mechanical powder inhalators conventionally used may be applied in the case that the effective ingredients are in powder form, and inhalators like a neblizer may be used in the case that the effective ingredients are in liquid form. As to the inhalation propellant, any one known in this field can be used, for example, fluorocarbon type compounds such as flon-11, flon-12, flon-21, flon-22, flon-113, flon-114, flon-123, flon-142c, flon-134a, flon-227, flon-C318, 1,1,1,2-tetrafluoroethane and the like; hydrocarbons such as propane, isobutane, n-butane and the like, ethers such as diethyl ether and the like; compressed gases, such as nitrogen gas, carbon dioxide gas and the like can be exemplified.

If necessary, the inhalant preparations of the present invention may be formulated with surface active agents, oils, seasonings, cyclodextrin or its derivatives and the like, accordingly. As to the surface active agents, there can be exemplified oleic acid, lecithin, diethylene glycol dioleate, tetrahydrofurfuryl oleate, ethyl oleate, isopropylmyristate, glyceryl trioleate, glyceryl monolaurate, glyceryl monooleate, gylyceryl monostearate, glyceryl monoricinoate, cetyl alcohol, stearyl alcohol, polyethylene glycol 400, cetyl pyridinium chloride, sorbitan trioleate (trade name: Span 85), sorbitan monooleate (trade name: Span 80), sorbitan monolauate (trade name: Span 20), polyoxyethylenated hardened castor oil (trade name: HCO-60), polyoxyethylene (20) sorbitan monolaurate (trade name: Tween 20), polyoxyethylene (20) sorbitan monooleate (trade name: Tween 80), lecithin derived from natural sources (trade name: Epikuron), oleyl polyoxyethylene (2) ether (trade name: Brij 92), stearyl polyoxyethylene (2) ether (trade name: Brij 72), lauryl polyoxyethylene (4) ether (trade name: Brij 30), oleyl polyoxyethylene (2) ether (trade name: Genapol 0-020), brock copolymer of oxyethylene with oxypropylene (trade name: Synperonic) and the like. As to the oils, corn oil, olive oil, cotton seed oil, castor oil and the like can be exemplified.

In case of making the effective ingredient of the present invention as a liquid form preparation, said effective ingredient may be dissolved in a liquid form carrier. As to the liquid form carriers, water, an aqueous solution of sodium chloride, an organic solvent and the like can be exemplified. Among these carriers, water is preferable. Further, in case of dissolving, a surface active agent such as polyoxyethylene glycol having molecular weight of 200 to 5000, polyoxyethylene (20) sorbitan monooleate and the like; sodium carboxymethyl cellulose, methyl cellulose, polyvinylpyrrolidon, polyvinyl alcohol or the like may be added thereto.

In case of making the effective ingredient of the present invention as in powder form, the ingredient may be pulverized in accordance with usual methods, for example, the ingredient is pulverized into refined powder, by mixing together with lactose, starch or the like so as to make it in a uniform mixture.

The amount of the effective ingredient to be contained in the therapeutical drug of the present invention is not specifically restricted. It can be selected from a wide range, usually it may be contained about 1 to 70% by weight in the desired pharmaceutical composition.

Administration methods of the therapeutical drug of the present invention is not specifically restricted. The therapeutical drug of the present invention can be administered according to the method of use, an age of the patient, distinction of sex, other conditions, condition of the symptoms and the like. For example, tablets, pills, liquids, suspensions, emulsions, granules, and capsules are orally administered. Injection preparations are intravenously administered singly or mixed with injection transfusions such as glucose solutions, amino acid solutions or the like; and if necessary, the injection preparations are administered singly intramuscularly, intracutaneously, subcutaneously, or intraperitoneally. Suppositories are administered into the rectum. The inhalants are administered into the cavity of mouth.

The dosage of the therapeutical drugs of the present invention is suitably selected according to the method of use, an age of the patient, distinction of sex, other conditions, condition of the symptoms and the like, and usually about 0.2 to 200 mg/kg of the body weight per day of the effective ingredient may be administered.

The agent for the treatment of COPD of the present invention possesses excellent improving effect on the deterioration of the pulmonary function, such as airflow obstruction, and exhibits extremely high curing effect against COPD.

The agent for the treatment of COPD of the present invention is a highly safe drug with less adverse side-effects such as nausia, vomiting, secretion of acid in the stomach.

EXAMPLES

The present invention will be explained in detail by illustrating the following Pharmaceutical Preparation Examples and Pharmacological Test Examples. However, the invention are not restricted to these examples.

In the following examples, "Compound A" means 6-[2-(3,4-diethoxyphenyl)thiazol-4-yl]pyridine-2-carboxylic acid.

| Pharmaceutical Preparation Example 1 | |
|---|---|
| Compound A | 150 g |
| Avicel (trade name, manufactured by Asahi Chemical Industry, Co., Ltd.) | 40 g |
| Corn starch | 30 g |
| Magnesium stearate | 2 g |
| Hydroxypropylmethyl celulose | 10 g |
| Polyethylene glycol-6000 | 3 g |
| Castor oil | 40 g |
| Ethanol | 40 g |

Compound A, Avicel, corn starch and magnesium stearate were mixed together and pulverized. The resulting mixture was subjected to form tablets by use of tableting machine having a punder of 10 mm in diameter. Then film coated tablets were prepared by coating with a film coating agent consisting of hydroxypropylmethyl cellulose, polyethylene glycol-6000, castor oil and ethanol.

| Pharmaceutical Preparation Example 2 | |
|---|---|
| Compound A | 150 g |
| Citric acid | 1.0 g |
| Lactose | 33.5 g |
| Dicalcium phosphate | 70.0 g |
| Pluronic F-68 | 30.0 g |
| Sodium laurylsulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dried sodium stearate | 3.0 g |
| Dried magnesium stearate | 3.0 g |
| Ethanol | q.s. |

Compound A, citric acid, lactose, dicalcium phosphate, Pluronic F-68 and sodium laurylsulfate were mixed together. The resulting mixture was sieved through No. 60 screen, then subjected to wet-granulation by using an alcohol solution containing polyvinyl pyrrolidone, Carbowax 1500 and 6000. If required, ethanol was added to the mixture to make it a lump in a paste form. Then corn starch was added thereto and mixing operation was continued until uniform particles were obtained. The resulting mixture was sieved through No. 10 screen, then the sieved mixture was placed on a tray and dried in an oven at 100° C. for 12 to 14 hours. Thus obtained dried particles were sieved through No. 16 screen, and dried sodium laurylsufate and dried magnesium stearate were added it with stirring. The resultant was compressed to form the desired shape by use of a tableting machine.

The core portion of the resulting tablets were treated with varnish, and talc powder were spread on the surface of the tablets so as to prevent it from moisture absorption. The under coat layer was coated around the core portion. Varnish coating were conducted with sufficient times, so as to make the tablets for oral administration. For the purpose to make the tablets to form complete spherical shape with smooth surface, further coating operations were conducted to give under coat layers and smooth surface coatings. Color coating were conducted until the obtained tablets had the desired surface coloring. After dried, the coated tablets were polished and had uniform luster.

| Pharmaceutical Preparation Example 3 | |
|---|---|
| Compound A | 5.0 g |
| Polyethylene glycol | 0.3 g |
| (Molecular weight: 4000) | |
| Sodium chloride | 0.9 g |
| Polyoxyethylene sorbitan monooleate | 0.4 g |
| Sodium metabisulfite | 0.1 g |
| Methyl paraben | 0.18 g |
| Propyl paraben | 0.02 g |
| Distilled water for injection | 10.0 ml |

The above-mentioned parabens, sodium metabisulfite and sodium chloride were dissolved in a half volume of the above-mentioned distilled water at 80° C. with stirring. Thus obtained solution was cooled to 40° C., then compound A, next polyethylene glycol and polyoxyethylene sorbitan monooleate were dissolved in the above-mentioned solution.

The remaining volume of the distilled water for injection was added to the obtained solution so as to adjust to the final volume, and the resulting solution was filtered and sterilized by use of a suitable filter paper, to prepared the desired injection preparation.

Pharmacological Test Example

In accordance with the method of Jun-ichi Fuchikami, et al. (Japanese Journal of Pharmacology, 2000, (82), p. 247), the following pharmacological test was conducted.

Hartley strain guinea pigs (5 weeks age, body weight: 300 to 379.5 g) were exposed to smoke of cigarette (trade name: Hi-Light, manufactured by Japan Tobacco Inc.) for 1 hour/day, 5 days a week, during 4 weeks, by using a flow-past type nose-only inhalation chamber, manufactured by Muenster Co. Control group as a normal group was exposed to the atmospheric air instead of cigarette smoke.

Compound A was suspended in 0.5% tragacanth gum aqueous solution, and this suspension was orally administered compulsorily to the guinea pigs (compound A administered group), in the amount of 10 mg/kg once a day, 1 hour before the exposure to cigarette smoke in the day of exposure, and in the morning in the day of non-exposure, respectively.

To the guinea pigs in the vehicle administered group, a 0.5% tragacanth gum aqueous solution without containing Compound A was orally administered instead of the suspension of compound A.

While, to the guinea pigs in the control group, neither the 0.5% tragacanth aqueous solution nor the compound A suspension were administered.

Before exposure and during the period of 4 weeks of exposure to the smoke of cigarette, the respiratory functions (specific airway resistance and peak expiration flow) of the guinea pigs were non-invasively assessed once a week under conscious condition, using Double-chamber Plethymograph method with a respiratory function measuring equipment (Pulmos-I, manufactured by M.I.P.S. Co.).

The respiratory functions (i.e., values of specific airway resistance and peak expiration flow) were obtained as an average of 100 times measured values of the functions, and were shown as the changes of percentage to the respective value of respiratory function measured before exposure to cigarette smoke.

The results are shown in Table 1 and Table 2 as follows.

TABLE 1

Changes in Specific airway resistance value

| Test groups | 1 Week after exposure (%) | 2 Week after exposure (%) | 3 Week after exposure (%) | 4 Week after exposure (%) |
|---|---|---|---|---|
| Control group | −3.23 ± 16.20 | −10.60 ± 17.94 | −4.35 ± 17.82 | 7.61 ± 21.57 |
| Vehicle administered group | 202.35 ± 65.10 * | 188.64 ± 58.07 * | 231.34 ± 67.33 ** | 216.57 ± 55.91 ** |
| Compound A administered group | 12.75 ± 7.45 # | 41.82 ± 26.91 # | 61.08 ± 29.27 # | 51.26 ± 24.28 # |

* P < 0.05,
** P < 0.01: Significant difference from Control group (Student's-test)
# P < 0.05: Significant difference from Vehicle administered group (Student's-test)

TABLE 2

Changes in Peak expiration flow

| Test groups | 1 Week after exposure (%) | 2 Week after exposure (%) | 3 Week after exposure (%) | 4 Week after exposure (%) |
|---|---|---|---|---|
| Control group | 10.31 ± 5.63 | 8.26 ± 10.15 | 17.33 ± 12.99 | 53.57 ± 21.32 |
| Vehicle administered group | −22.57 ± 4.83 ** | −10.44 ± 6.90 | −2.09 ± 4.48 | 26.26 ± 5.54 |
| Compound A administered group | 9.67 ± 8.48 ## | 15.67 ± 14.98 # | 14.08 ± 8.48 | 37.06 ± 11.33 |

** P < 0.01: Significant difference from Control group (Student's-test)
## P < 0.01: Significant difference from Vehicle administered group. (Student's-test)

As is clearly indicated in the above-mentioned Tables 1 and 2, compound A exhibited excellent improving effects in both parameters of the specific airway resistance and peak expiration flow, as compared with those obtained in the vehicle administered group. Thus, it is clearly shown that the compound A possesses the improving effect on deteriorating the pulmonary function.

The invention claimed is:

1. A method for treating chronic obstructive pulmonary disease, which comprises administering to a person in need thereof a medicament containing, as the effective ingredient, at least one compound selected from the group consisting of thiazole compounds and salts thereof represented by the general formula (1),

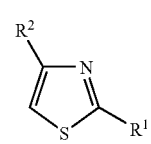

(1)

wherein $R^1$ is a phenyl group which may have 1 to 3 lower alkoxy groups as substituents on the phenyl ring; and $R^2$ is a pyridyl group which may have 1 to 3 carboxyl groups as substituents on the pyridine ring.

2. The method of claim 1, wherein the at least one thiazole compound is 6-[2-(3,4-diethoxyphenyl)-thiazol-4-yl]pyridine-2-carboxylic acid.